US010398316B1

(12) United States Patent
Betts-Lacroix et al.

(10) Patent No.: US 10,398,316 B1
(45) Date of Patent: Sep. 3, 2019

(54) METHOD AND APPARATUS FOR DETERMINING PHYSIOLOGICAL CHARACTERISTICS OF EXPERIMENTAL ANIMALS BASED UPON INFRARED AND VISIBLE LIGHT IMAGES

(71) Applicant: Vium, Inc., San Mateo, CA (US)

(72) Inventors: Jonathan Noble Betts-Lacroix, Belmont, CA (US); Timothy Robertson, Belmont, CA (US); Laura Schaevitz, Los Gatos, CA (US); Kyle Heath, San Francisco, CA (US)

(73) Assignee: Vium, Inc., San Mateo, CA (US)

(*) Notice: Subject to any disclaimer, the term of this patent is extended or adjusted under 35 U.S.C. 154(b) by 225 days.

(21) Appl. No.: 15/282,549

(22) Filed: Sep. 30, 2016

(51) Int. Cl.
| | | |
|---|---|---|
| *A61B 5/117* | (2016.01) | |
| *A61B 5/01* | (2006.01) | |
| *G06T 7/00* | (2017.01) | |
| *H04N 5/33* | (2006.01) | |
| *H04N 5/247* | (2006.01) | |
| *A61B 5/00* | (2006.01) | |
| *A61B 5/02* | (2006.01) | |

(52) U.S. Cl.
CPC .............. *A61B 5/01* (2013.01); *A61B 5/0077* (2013.01); *A61B 5/02007* (2013.01); *A61B 5/448* (2013.01); *G06T 7/0014* (2013.01); *H04N 5/247* (2013.01); *H04N 5/332* (2013.01); *A61B 2503/40* (2013.01); *A61B 2503/42* (2013.01); *G06T 2207/10016* (2013.01); *G06T 2207/10048* (2013.01); *G06T 2207/30088* (2013.01); *G06T 2207/30096* (2013.01)

(58) Field of Classification Search
None
See application file for complete search history.

(56) References Cited

U.S. PATENT DOCUMENTS 6,751,340 B2* 6/2004 Prokoski .............. A61B 5/1176
348/14.09
10,064,392 B1 9/2018 Betts-Lacroix

OTHER PUBLICATIONS

Wang, Chun-Kai. "Multiple Mice Tracking Using Microsoft Kinect." Diss. Massachusetts Institute of Technology, 2013 (available at http://hdl.handle.net/1721.1/85517).
Viola, R and Jones, M. "Robust Real-time Object Detection." Cambridge Research Laboratory Technical Support Series, CRL2001/01, Feb. 2001 (available at http://www.hpl.hp.com/techreports/Compaq-DEC/CRL-2001-1.pdf).
(Continued)

*Primary Examiner* — Brian T Gedeon
(74) *Attorney, Agent, or Firm* — Nienstadt PLLC

(57) ABSTRACT

A method for determining at least one physiological characteristic of at least one experimental animal in a cage is disclosed. The method may include capturing at least one infrared image of the at least one experimental animal in a band of infrared radiation that is within the range of from about 3 μm to about 14 μm in wavelength and capturing at least one visible image of the at least one experimental animal. The method may further include correlating the at least one image and the at least one visible light image and determining the at least one physiological characteristic of the at least one experimental animal based at least in part on the correlation. An apparatus to determine at least one physiological characteristic of at least one experimental animal is also disclosed.

21 Claims, 13 Drawing Sheets

(56) References Cited

OTHER PUBLICATIONS

Branson, K. et al. Tracking Multiple Mouse Contours (Without Too Many Samples). 2005 IEEE Computer Society Conference on Computer Vision and Pattern Recognition (CVPR '05).

Stauffer, C., and W.E.L. Grimson. "Adaptive Background Mixture Models for Real-time Tracking." Proceedings. 1999 IEEE Computer Society Conference on Computer Vision and Pattern Recognition (Cat. No. PR00149).

Dalai, N., and B. Triggs. "Histograms of Oriented Gradients for Human Detection." 2005 IEEE Computer Society Conference on Computer Vision and Pattern Recognition (CVPR '05).

Ohayon, S. et al. (2013). Automated Multi-day Tracking of Marked Mice for the Analysis of Social Behaviour. Journal of Neuroscience Methods, 219(1), 10-19.

Xu, C. et al. "Estimate Hand Poses Efficiently from Single Depth Images." International Journal of Computer Vision Int J Comput Vis 116.1 (2015): 21-45.

Bourdev, L et al. "Poselets: Body part detectors trained using 3d human pose annotations." 2009 IEEE 12th International Conference on Computer Vision. IEEE, 2009.

Felzenszwalb, P. F., et al. "Object detection with discriminatively trained part-based models." IEEE transactions on pattern analysis and machine intelligence 32.9 (2010): 1627-1645.

Sanchez, B. M. et al. (2008). "Use of a portable thermal imaging unit as a rapid, quantitative method of evaluating inflammation and experimental arthritis." Journal of Pharmacological and Toxicological Methods, 57(3), 169-175.

Jasemian, Y. (2011). "Refinement of the Collagen Induced Arthritis Model in Rats by Infrared Thermography." BJMMR British Journal of Medicine and Medical Research, 1(4), 469-477).

Al-Noori, S. et al. "Brown Adipose Tissue Thermogenesis Does Not Explain the Intra-administration Hyperthermic Sign-reversal Induced by Serial Administrations of 60% Nitrous Oxide to Rats." Journal of Thermal Biology 60 (2016): 195-203.

Smriga, M. et al. "Use of Thermal Photography to Explore the Age-dependent Effect of Monosodium Glutamate, NaCl and Glucose on Brown Adipose Tissue Thermogenesis." Physiology & Behavior 71.3-4 (2000): 403-07.

Faustino-Rocha, A.I. et al. "Ultrasonographic, Thermographic and Histologic Evaluation of MNUinduced Mammary Tumors in Female Sprague-Dawley Rats." Biomedicine & Pharmacotherapy 67.8 (2013): 771-76.

Poljak-Blazi, M. et al. "Specific Thermographic Changes During Walker 256 Carcinoma Development: Differential Infrared Imaging of Tumour, Inflammation and Haematoma." Cancer Detection and Prevention 32.5-6 (2009): 431-36.

Gordon, C. J. (1993). Temperature Regulation in Laboratory Rodents. Cambridge: Cambridge University Press.

U.S. Appl. No. 15/282,472, filed Sep. 30, 2016, to Betts-Lacroix et al.

U.S. Appl. No. 15/280,565, filed Sep. 29, 2016, to Harada et al.

* cited by examiner

METHOD AND APPARATUS FOR DETERMINING PHYSIOLOGICAL CHARACTERISTICS OF EXPERIMENTAL ANIMALS BASED UPON INFRARED AND VISIBLE LIGHT IMAGES

TECHNICAL FIELD

This application relates to methods and apparatuses for facilitating animal research.

BACKGROUND

Research is commonly performed on experimental animals that are housed in cages. Typically, these experimental animals are small mammals, such as mice or rats. The research may involve, for example, a drug test, a nutritional test, a genetic test, a test of a surgical procedure, an optogenetics test, or another observation of a physiological or behavioral response to a change in environmental condition or other stimulus. The experimental animals may be divided into a control group and one or more experimental groups. The cages in which the animals are housed may be arrayed, such as in racks.

The housed animals are typically checked in at least two ways: husbandry checks and experimental checks. Husbandry refers to serving the physiological needs of the animals. Husbandry may include observing the wellbeing of the animals, such as, for example, a health check once or twice a day to make sure that none of the animals has developed any symptoms of disease or has died. Health checks may involve looking at the animals through the transparent cage walls in situ without moving the cages, or alternatively pulling the cages partially or completely out of their racks to visually inspect the animals. Experimental checks, meanwhile, are performed to obtain data for the research being conducted. Experimental checks may involve closer examination of the animals than husbandry checks, such as involving opening the cages and removing the animals from the cages. Experimental checks may involve, for example, looking for clinical symptoms in the animals. Experimental checks may also include behavioral tests, such as, for example, water maze or hole board tests, extractions of blood or tissue from the animals, or measurements, such as imaging of the animals.

However, physically contacting the animals, such as through opening the animals' cages, removing them from their cages, and performing measurements on them—or even just approaching the cage to view the animal through the bidirectionally transparent wall, or partially sliding the cage containing the animal out of a rack—can physiologically or psychologically perturb the animals. The consequences of these types of perturbations are often not well understood. Furthermore, there may be inconsistencies in the perturbations, such as differences in when and how the human technicians perform checks across different individual animals. The animals' physiological states and behavior may therefore be altered in ways that are difficult to predict and inconsistent between distinct animals. Thus, these measurement techniques can interfere significantly with the quality of the data obtained from the experiment.

The process of checking the experimental animals may also cause contamination of the animal's living space or the testing equipment. This contamination may, in turn, exacerbate the differences in conditions under which the animals are housed. For example, one human technician may introduce one particular foreign odor into one living space, while another human technician introduces a different odor into another living space. The human technicians who are handling animals from different cages, or using common equipment, may also cause cross-contamination between animals in different cages. In addition, a substantial amount of resources, such as the time and labor of skilled technicians, is expended to monitor the animals. This can account for a significant amount of the total cost of running such an experiment.

Thus, it is desirable to perform checks on experimental animals to experimental animals in a way that yields rich, high-resolution, and reliable data in relation to the number of animals. It is also desirable to avoid physical contact with the animals, inconsistent perturbations of the animals, and cross-contamination between animals in different cages when the animals are checked. Moreover, it is desirable to reduce the amount of time and labor that is expended on running animal experiments.

Thus, it would be desirable to have processes and systems to determine physiological characteristics of experimental animals without or with minimal human technician effort, time, and handling and/or direct observation of experimental animals. It would be desirable for such processes and systems to be efficient, reproducible, and/or relatively inexpensive.

Experimental animals may be monitored, at least in part, by various image capture devices within or outside cages. However, providing image capture devices within cages presents potential issues regarding possible contamination of, decreased lifespan of, and/or increased repair or maintenance such image capture devices. And, providing a set of image capture devices for each cage may be expensive, decreasing the economic efficiency of monitoring experimental animals via image capture devices en masse. Furthermore, certain plastic and other type of cages commonly used to house and monitor experimental animals may include walls that are transparent to visible light, but not transparent to infrared light.

Thus, it would be desirable to have experimental animal cages and monitoring systems that are, at least in part, transparent to infrared light, while at the same time are efficient to use, reproducible, and/or relatively inexpensive.

SUMMARY

In one embodiment, a method for determining at least one physiological characteristic of at least one experimental animal in a cage is provided. The method may include capturing at least one infrared image of the at least one experimental animal in a band of infrared radiation that is within the range of from about 3 µm to about 14 µm in wavelength, and capturing at least one visible image of the at least one experimental animal. The method may further include correlating the at least one image and the at least one visible light image, and determining the at least one physiological characteristic of the at least one experimental animal based at least in part on the correlation.

The step of capturing at least one infrared image may include capturing multiple video frames that depict temperatures of the at least one experimental animal, and the step of capturing at least one visible image of the at least one experimental animal may include capturing multiple video frames that depict visible light.

The at least one experimental animal may be a rodent.

The step of capturing the at least one infrared image and the step of capturing the at least one visible image occur both occur within a span of 0.1 seconds.

The step of correlating the at least one infrared image and the at least one visible light image may further include determining a position of at least one part of the at least one experimental animal in the at least one visible light image, and determining a part temperature of the at least one part of the at least one experimental animal based on data from the at least one infrared image.

The step of determining the at least one at least one physiological characteristic may include assessing a degree of hair loss of the at least one experimental animal, assessing a degree of tumor vascularization at the at least one part of the at least one experimental animal, assessing a degree of brown adipose tissue thermogenesis occurrence at the at least one part of the at least one experimental animal, and/or determining a core temperature of the at least one experimental animal.

The step of determining the part temperature may further include using a thermal reference captured in the at least one infrared image to calibrate a temperature scale of the at least one infrared image.

The step of determining the part temperature may further include adjusting a temperature provided in the at least one infrared image based on at least one of a distance of the position from a camera that captured at least one infrared image and an angle of the at least one part of the experimental animal with respect to the camera.

In another embodiment, an apparatus to determine at least one physiological characteristic of at least one experimental animal is provided. The apparatus may include a cage housing the at least one experimental animal. The cage may include at least one wall with a window that is transparent to a band of infrared radiation that is within the range of from about 3 μm to about 14 μm in wavelength. The apparatus may further include a first image capture device configured to capture at least one infrared image of the at least one experimental animal through the transparent window, a second image capture device configured to capture at least one visible light image of the at least one experimental animal, and a controller. The controller may be configured to receive the at least one infrared image, receive the at least one visible light image, and determine the at least one physiological characteristic of the at least one experimental animal using the at least one infrared image and the at least one visible light image.

The second image capture device may be further configured to capture the at least one visible light image through the transparent window. The transparent window may comprise and or substantially consist of NaCl.

The at least one visible light image may include multiple video frames that depict captured visible light, and the at least one infrared image may include multiple video frames that depict temperatures of the at least one experimental animal.

The controller may be further configured to determine a position of at least one part of the at least one experimental animal using the at least one visible light image, and use at least the data from the at least one infrared image and the determined position of the at least one part of the at least one experimental animal, to determine at least one physiological characteristic of the at least one experimental animal.

The at least one physiological characteristic may include a degree of hair presence, a degree of tumor vascularization, a degree of brown adipose tissue thermogenesis occurrence, and/or a core temperature of the at least one experimental animal.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and aspects of the apparatuses and methods described herein and, together with the description, serve to explain the principles of the invention.

DETAILED DESCRIPTION

An electronic monitor may be adapted to be removably coupled to a cage housing experimental animals to be positioned in a predefined position relative to the cage and monitor one or more of the experimental animals. The electronic monitor can be adapted to maintain a substantially sterile barrier between the animal living space in the cage and the environment external to the cage while the electronic monitor is coupled to the cage. Sterility refers to chemical and biological isolation from the ambient environment, such as, for example, isolation from foreign odors, soot particles, viruses, parasitic worm eggs, bacteria, prions, proteins, metabolites, parasitic mites and their eggs, and humidity and temperature fluctuations. The electronic monitor can thereby monitor the experimental animals while minimizing perturbations to the animals. Examples of such an electronic monitor and other related experimental animal monitoring instrumentalities are described in U.S. patent application Ser. No. 14/549,403 to Betts-LaCroix et al., U.S. patent application Ser. No. 14/788,749 to Heath et al., and U.S.

patent application Ser. No. 14/871,966 to Betts-LaCroix et al., which are incorporated herein by reference in their entireties.

Multiple animals that are under the same experimental conditions may be selected to be housed in the same cage. For example, animals in a control group may be housed together, while animals in a particular experimental group may be housed together. When animals that are under the same experimental conditions are housed in the same cage, it may not be necessary for electronic monitor 200 to track the individual identities of the animals, though that is also contemplated by this disclosure. Rather, since the mice may be treated as experimentally identical, aggregated or averaged information relating to all of the mice in a particular cage may suffice for purposes of the experiment.

Figure 3A:
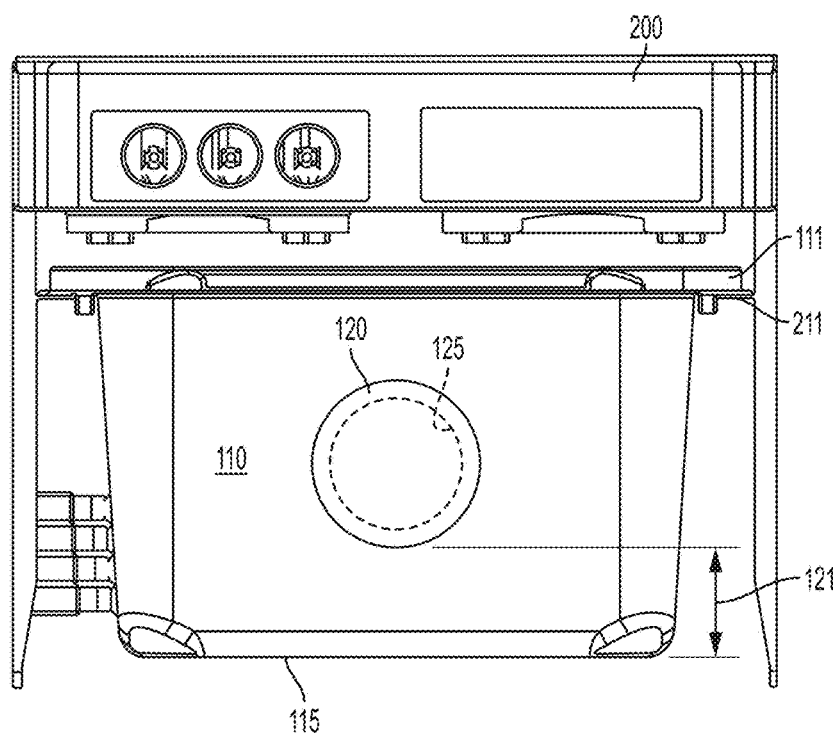
FIG. 3A is a front view of an example of the cage embodiment of FIGS. 1A and 1B connected to an electronic monitor.

FIG. 3A illustrates an example of an embodiment of an electronic monitor 200 and a cage 100 that is coupled thereto. Cage 100 has one or more walls 110 that enclose a living space for experimental animals. In one embodiment, walls 110 define a living space that is approximately a rectangular prism. In other embodiments, however, walls 110 may have other shapes or dimensions. In illustrative examples, a mouse cage may be shaped and sized to house from one to about five mice, while a rat cage may be capable of housing up to about 10 mice. For example, mice may be housed singly or in pairs. In one embodiment, walls 110 of cage 100 enclose a substantially cuboid living space 145 of at least 10 cm×10 cm×5 cm. In various embodiments, cage 100 may have a volume less that 60 liters, less than 20 liters, and/or less than 10 liters. In various embodiments, wall 110 may have a thickness of less than 0.1 mm, 0.25 mm, 0.1 mm to 0.5 mm, 0.5 mm to 5 mm, and/or more than 5 mm. While thinner cages may be lighter and cheaper, thicker cages may be stronger and more robust. Cage 100 may comprise or consist essentially of a plastic material or materials, for example, Polycarbonate, PET, PETG, Polystyrene, Polypropylene, Polysulfone, or alloys, derivatives, or copolymers based on the same.

Cage 100 may further comprise cage floor 115 and one or more protruding lip 111. By one or more lip 111 of cage 100 and one or more support flanges 211 of electronic monitor 200, cage 100 may be securely coupled to electronic monitor 200. Electronic monitors 200 may be structurally adapted to permit easy and fast uncoupling of cages 100 from electronic monitors 200 by a human technician or even by a robot. For example, electronic monitors 200 may be structurally adapted to permit coupling and uncoupling by sliding cages 100 into and out of electronic monitors 100. To that effect, via protruding one or more lip 111 and one or more support flanges 211 of electronic monitor 200, cage 100 may be securely mounted within electronic monitor 200.

Cage 100 may also include shaped features to provide water and/or food to the experimental animals. For example, cage 100 may have a water dispenser and/or a food dispenser. If cage 100 is of a disposable type, then water dispenser and/or food dispenser may be pre-filled with an amount of water or food corresponding to an expected lifespan of the animals, an expected timespan of an experiment, or a given interval between cage changes. A given interval between cage changes may be, for example, one, two, or four weeks, such as may be suitable for the particular types of cage, animal, and experiment.

Figure 1A:
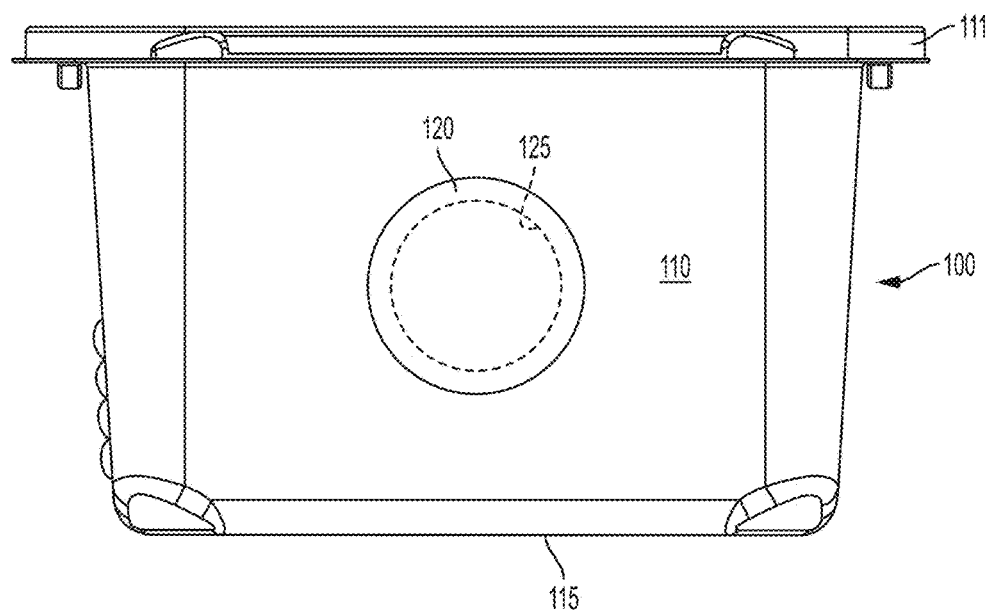
FIGS. 1A and 1B are front and perspective views, respectively, of an example of an embodiment of a cage with a thermographically transparent window.
Figure 1B:
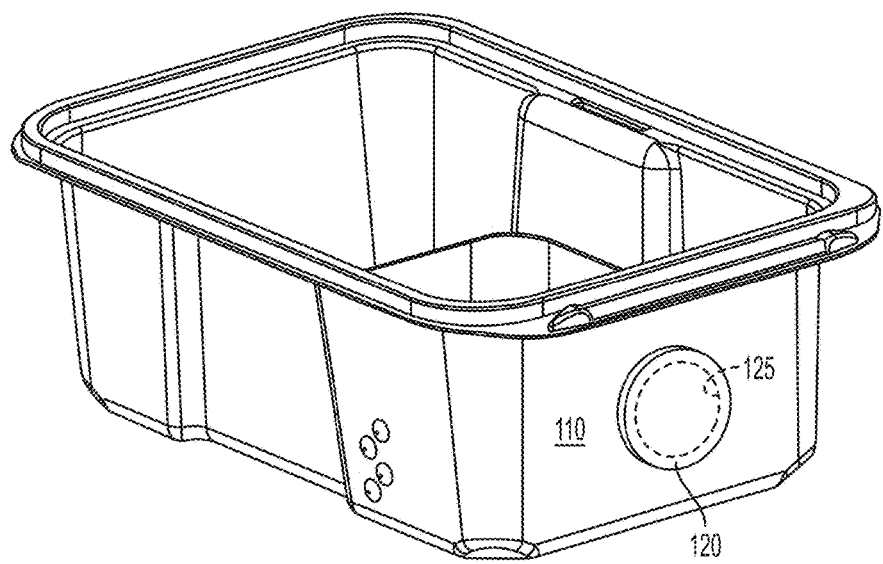

As depicted in further detail in FIGS. 1A and 1B, at least one wall 110 of cage 100 may include at least one window 120. In exemplary embodiments, window 120 may be thermographically transparent such that thermographic images may be captured through it. For example, window 120 may be transparent to a band of infrared radiation that is within the range of from about 3 µm to about 14 µm in wavelength. In other words, window 120 may be substantially transparent to wavelengths between approximately 3 µm and approximately 14 µm. Window 120 may, in some embodiments, may include or consist essentially of ZnCl or NaCl. In exemplary embodiments, at least the inner side of window 120 that is exposed to the living area of cage 100 comprises a non-toxic material, such as NaCl. In other exemplary embodiments, at least the inner side of window 120 may be covered with a hard carbon coating such as the "Diamond-Like Coating" produced by Tydex. Use of a non-toxic material may prevent adverse health effects and/or compromised experimental data if an experimental animal ingests some the window 120 material. Further, use of a non-toxic material on the inner side of window 120 may permit window 120 to substantially consist of a lower cost material. In various embodiments, window 120 may have a thickness of less than 0.1 mm, 0.25 mm, 0.1 mm to 0.5 mm, 0.5 mm to 5 mm, and/or more than 5 mm.

Wall 110 may include an aperture 125 covered by window 120 such that infrared light may pass through that portion of wall 110. In various embodiments, aperture 125 may be integrally formed during molding of cage 100, or may be created via punching, drilling, melting, sanding, or the like of a portion of wall 110. For example, as shown in FIGS. 1A and 1B, the surface area of window 120 may be greater than the size of aperture 125. In this manner, window 120 may be secured to the portion of wall 110 surrounding aperture 125. In embodiments where window 120 is positioned on the outside surface of wall 100 (e.g., outside the living area), an outer portion of the inner surface of window 150 (e.g., facing the living area) may affixed to portions of the outer surface of wall 110 with an adhesive material, such as a non-toxic glue. The portions of the outer surface of wall 110 to which window 120 is affixed may be a plastic material. Conversely, in embodiments where window 120 is positioned on the inside surface of wall 100 (e.g., inside the living area), an outer portion of the outer surface of window 150 (e.g., facing away from the living area) may affixed to portions of the inner surface of wall 110 with an adhesive material, such as a non-toxic glue. The portions of the inner surface of wall 110 to which window 120 is affixed may be made of a plastic material.

Figure 2A:
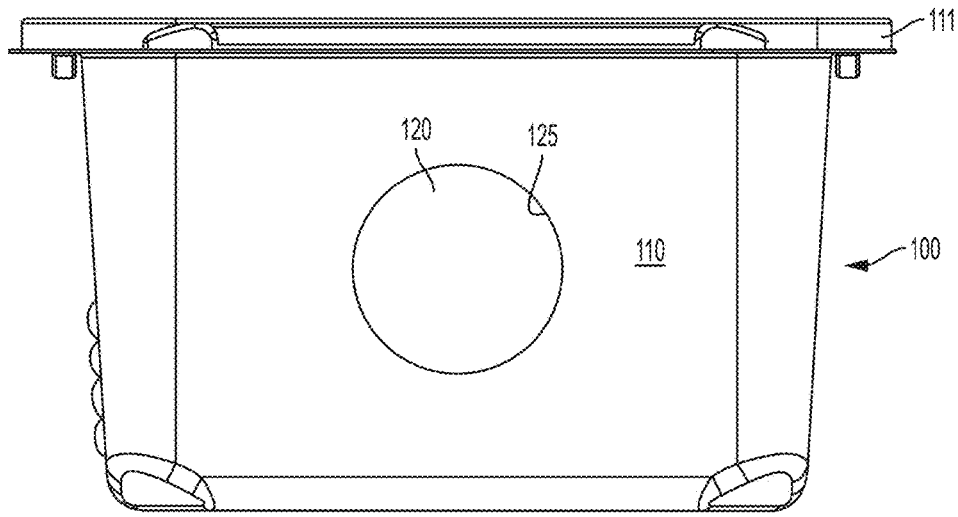
FIGS. 2A and 2B are front and perspective views, respectively, of an example of another embodiment of a cage with a thermographically transparent window.
Figure 2B:
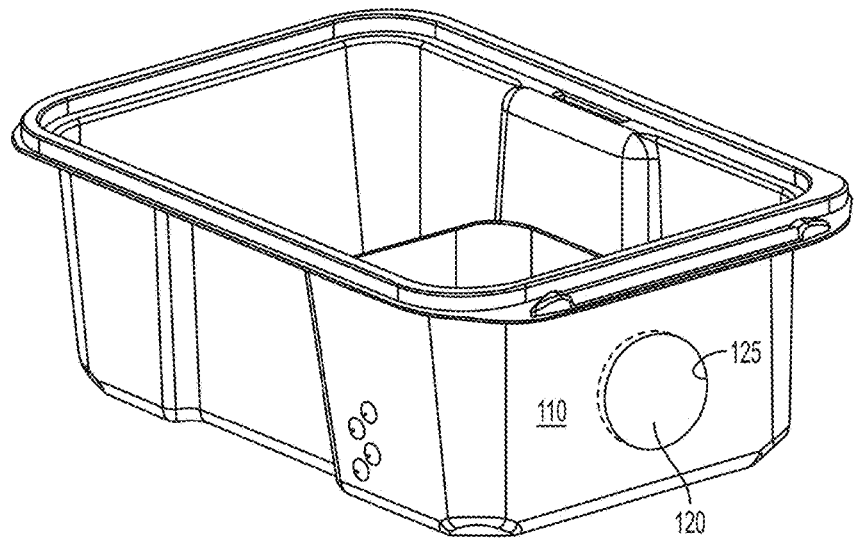

With reference to FIGS. 2A and 2B, window 120 may be fitted at least partially within aperture 125. Window 120 may be maintained within aperture 125 via interference fit and/or an adhesive material.

Figure 3B:
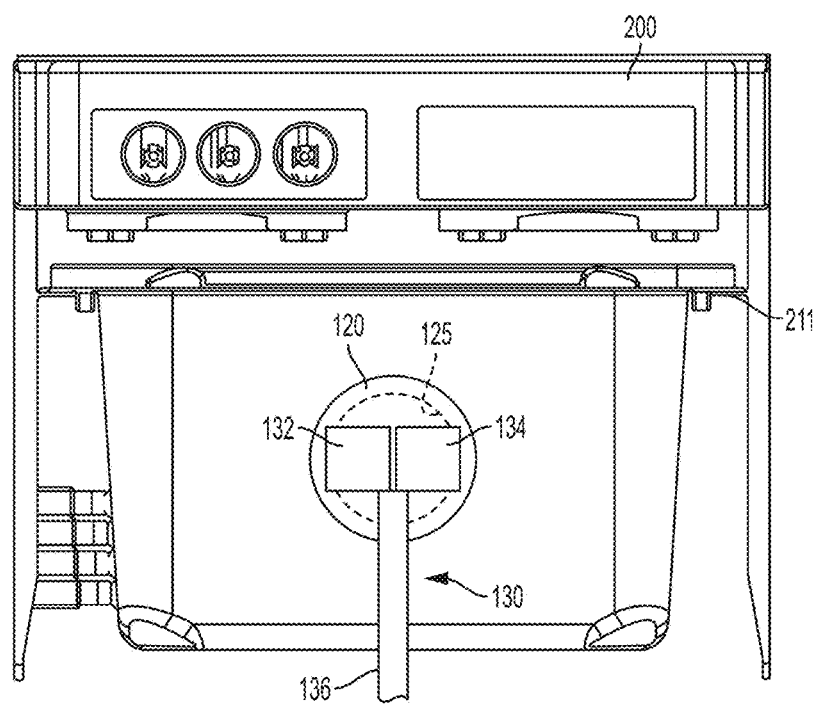
FIG. 3B is a front view of the cage embodiment of FIG. 3A, in which two image capture devices are aligned with the thermographically transparent window.

FIG. 3B depicts the system of FIG. 3A, but also includes camera system 130. As shown, camera system 130 may include a thermographic infrared camera 132 and a visible light camera 134. Cameras 132, 134 may be configured to capture still images and/or video images and may be supported by camera support 130. In embodiments where multiple cages 100 and electronic monitors 200 are supported by a rack, camera support 136 may be configured to move such that camera system 130 may be used to sequentially capture images of experimental animals in various cages 100 within the rack. In other embodiments, each cage 100 or electronic monitor 200 may correspond to a camera system 130. In some embodiments, visible light camera 134 may capture image(s) through a transparent portion of wall 110, for example a portion of wall 110 adjacent to or otherwise near window 120.

It is contemplated that window 120 be disposed within wall 110 at a height to reduce or eliminate the likelihood that an experimental animal may lick, touch, or otherwise contact window 120. Similarly, it is contemplated that window 120 be positioned to provide an optimal viewing angle of experimental animals in cage 100 for image capture devices 132, 134. Thus, with reference to FIG. 121, the bottom of aperture 125 may be a distance 121 from cage floor 115 of cage 100. In various embodiments, distance 121 may be at least 25 cm, at least 15 cm, or at least 6 cm. It is also contemplated that window 120 be disposed within wall 110 in a position sufficiently far from lip 111 and/or the top of wall 110 to prevent possible interference, mechanical or otherwise, between aperture 125 or window 120 and electronic monitor 200. Thus, in various embodiments, a distance from the top of aperture 125 may at least 5 cm from lip 111 or the top of cage.

Figure 8:
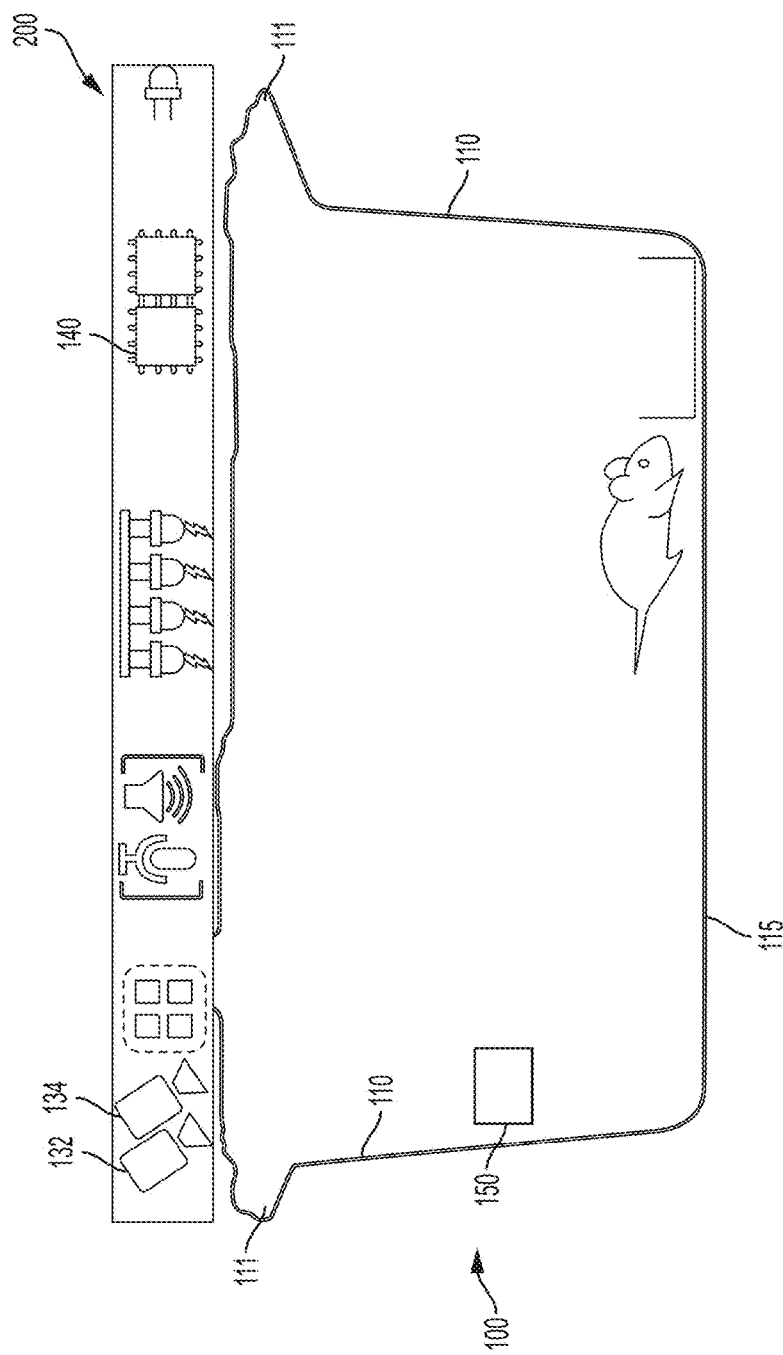
FIG. 8 is a schematic illustration of a side view of an example of an embodiment of a cage connected to an electronic monitor with a set of image capturing devices.

FIG. 8 depicts an alternative embodiment of cage 100 and electronic monitor 200 in which electronic monitor 200 includes an infrared camera 132 and a visible light camera 134. In such embodiments, electronic monitor 200 may accomplish the functions of camera system 130 described above. In such embodiments, a thermographically transparent window 120 may be omitted from cage 100.

In yet other alternative embodiments, infrared camera 132 may be included within electronic monitor 200 and visible light camera 134 may be positioned to view cage 100 and its contents through wall 110 without window 120. And in yet other alternative embodiments, visible light camera 134 may be included within electronic monitor 200 and infrared camera 132 may be positioned to view cage 100 and its contents through window 120. In yet other embodiments, one or more cameras 132, 134 may be provided within cage 100; such cameras may, for example, transmit data and receive power through one or more electrical feedthroughs, such as those disclosed in U.S. patent Ser. No. 15/280,565, filed Sep. 29, 2016, which is incorporated herein by reference in its entirety.

In yet other alternative embodiments, window 120 may be omitted and infrared camera 132 may capture images through aperture 125. The escape of experimental animals through aperture 125 may be prevented by, for example, a high placement of aperture 125, making aperture 125 too small for the experimental animal to fit through, or blocking aperture 125 with a protective lens or other element of infrared camera 132.

Figure 4:
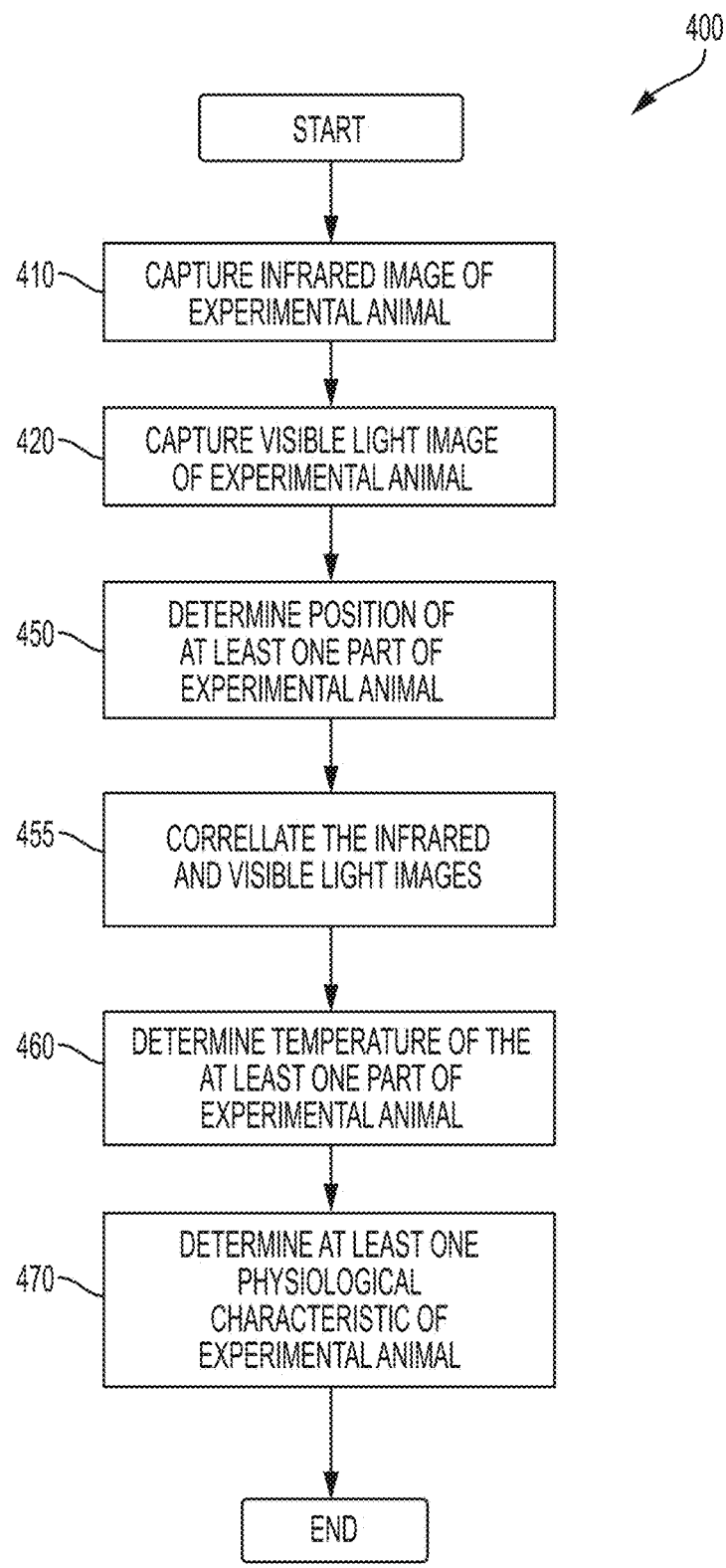
FIG. 4 is a flowchart of an example of a method of determining at least one physiological characteristic of an experimental animal.

FIG. 4 is a flowchart of an exemplary embodiment of a method of using infrared camera 132 and visible light camera 134 to determine at least one physiological characteristic of an experimental animal. Infrared camera 132 and visible light camera 134 may be controlled by and may provide captured imagery to a controller 140. Infrared camera 132 may for example, may be configured to capture images based on a band of infrared radiation that is within the range of from about 3 μm to about 14 μm in wavelength. This disclosure further contemplates that any other type of suitable thermographic camera may serve as infrared camera 132.

Controller 140 may be adapted to largely or wholly automate the operation of infrared camera 132 and visible light camera 134, as well as control the movement of camera support 136. Controller 140 may accomplish the data processing steps discussed below, including but not limited to any image processing, position-determining, calibration, temperature adjustment, calculation, lookup, interpolation, and/or physiological or metabolic characteristic determining steps discussed herein.

Furthermore, controller 140 may serve other functions, as explained in the patent applications incorporated by reference above (with respect to "controller 320" in such applications). For example, controller 140 may further control the operation of electronic monitors 200, control user interfaces to interface with a human supervisor, and/or interface with an external server or network. Controller 140 may automatically control one or more aspects of operation of electronic monitor 200 and may be adapted to largely or wholly automate the operation of electronic monitor 200. The controller may, for example, receive inputs from a human user, provide instructions to other components of monitor 200, perform processing of data received from any or all of ambient sensors, atmospheric sensors, electromagnetic detectors, cameras 132, 134, a compound releasing system, acoustic sensors, and a weight scale, and/or output signals, such as alerts or other indicators. Controller 140 may be adapted, for example, to receive signals from ambient sensors, atmospheric sensors, cameras 132, 134, other electromagnetic detectors, acoustic sensors 280, and weight scale; to transmit control signals to electromagnetic sources 270 to provide electromagnetic radiation into the living space; to transmit signals to an acoustic emitters; to transmit signals to user interfaces; or transmit and receive signals to a compound releasing.

Controller 140 may include one or more microprocessors, controllers, processing systems, computers, and/or circuitry, such as any combination of hardware or software modules. Components of controller 140 may be distributed across one or more different physical locations and these components may communicate with each other to perform the operations of controller 140. For example, components of controller 140 may be physically located in the individual electronic monitors 200 and/or at remote client devices such as personal computers or handheld devices. Controller 140 may be implemented in any quantity of hardware components, such as including Raspberry Pi, an integrated circuit such as, for example, an application-specific integrated circuit (ASIC), field-programmable gate array (FPGA), or "system on a chip" (SoC), and/or other processor, memory, bus, input/output, or communications systems. Furthermore, some or all of these hardware components may be located locally or remotely. For example, controller 140 may be implemented partially or entirely through cloud computing. Controller 140 may operate any commercially available operating system software, including, for example, Linux, Windows, MacOS, iOS, Android, Unix, OS/2, or any other commercially available and/or custom software. For example, controller 140 may operate customized animal-monitoring and signal-processing software. Furthermore, controller 140 may include one or more types of input devices, such as for example a touchpad, keyboard, button panel, mouse, microphone, or voice recognition device.

In some embodiments, controller 140 may govern disclosed processes with respect to a single cage 100, in which case controller 140 may be disposed within electronic monitor 200. In other embodiments, a controller 140 may govern disclosed processes with respect to a plurality of cages 100, for example, a plurality of cages 100 supported by a single rack or a plurality of cages 100 supported by a multiple racks in a single vivarium.

Controller 140 may be adapted to process received data and/or human inputs to determine values of one or more metrics relating to experimental animals or their living space. The metrics may include one or more physiological, behavioral, or environmental characteristics. Physiological metrics or characteristics may include, for example, respiration rate, health check, heart rate, body weight, thinness, body temperature, metabolism, coat characteristics such as rough hair coat, stress level, a Body Condition Score ("BCS"), alopecia, fever, inflammation, arthritis, whether the animal is dead, ataxia or another central nervous system (CNS) disorder, circling or head tilt, dehydration, dermatitis, distended abdomen, dyspnea, dystocia, ear problems, emaciation, eye problems, fight wounds, hunched posture, hydrocephalus, irregular gait, lesions, lethargy, listlessness, malocclusion, necropsy, the number of animals in a cage, paleness of color, the presence of post-operative staples, prolapse, pruritus, seizure, other sickness, brown adipose tissue thermogenesis, metabolic characteristics, the presence of a tumor, and/or a degree of tumor vascularization.

Figure 5B:
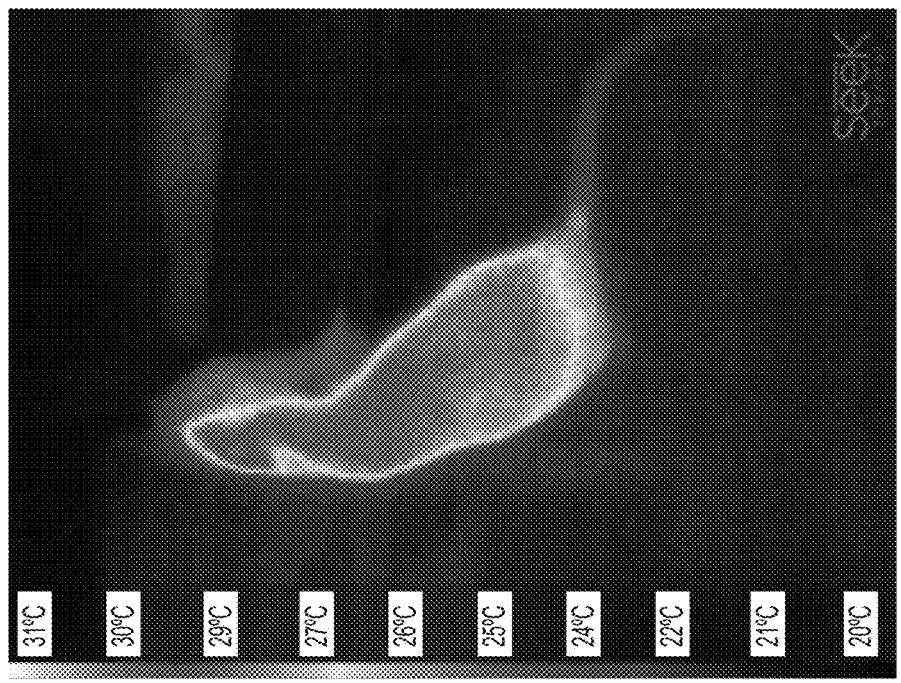
FIGS. 5A and 5B are a pair of corresponding infrared and visible light images, respectively, of an experimental animal in a cage, consistent with disclosed embodiments.
Figure 6B:
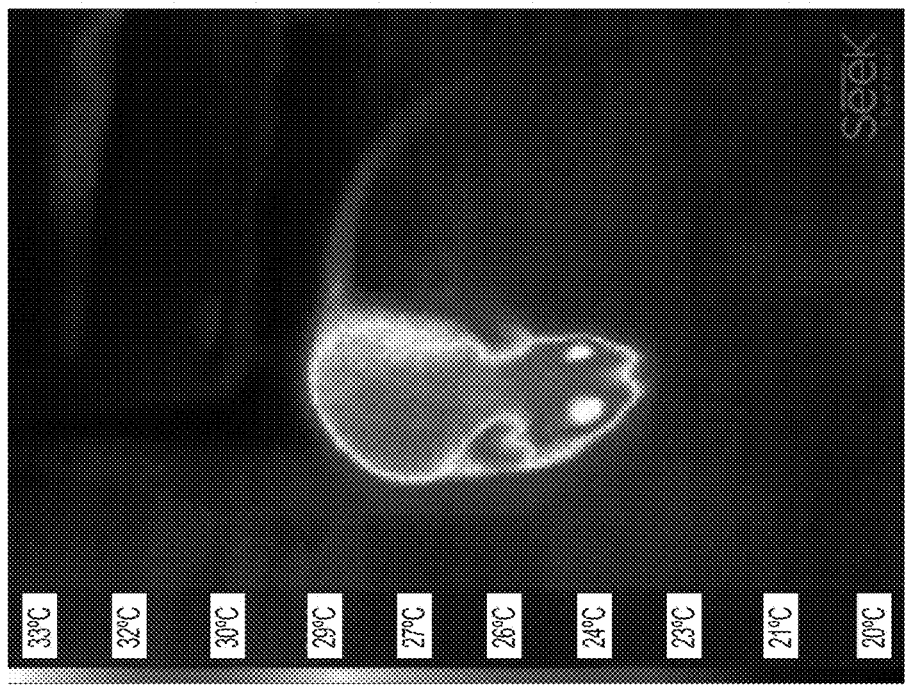
FIGS. 6A and 6B are another pair of corresponding infrared and visible light images, respectively, of an experimental animal in a cage, consistent with disclosed embodiments.
Figure 7A:
FIGS. 7A to 7G are corresponding infrared and visible light images and annotations thereupon that illustrate identification of a position of parts of an experimental animal and determination of a temperature of such parts, consistent with disclosed embodiments.
Figure 7B:
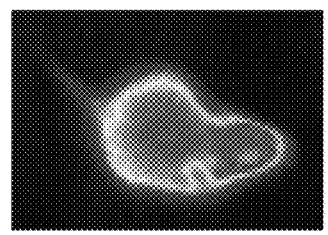

As in step 410, an infrared image of an experimental animal may be captured with infrared camera 132. The infrared image may be captured through the side of cage 100, for example through a window 120 as described above and depicted in FIG. 3B. In other embodiments, the infrared image may be captured from above, for example from an infrared camera 132 mounted within electronic monitor 200, as depicted in FIG. 8. FIGS. 5B, 6B, and 7B each provide an illustrative infrared image of an experimental animal in a cage taken from above.

Figure 5A:
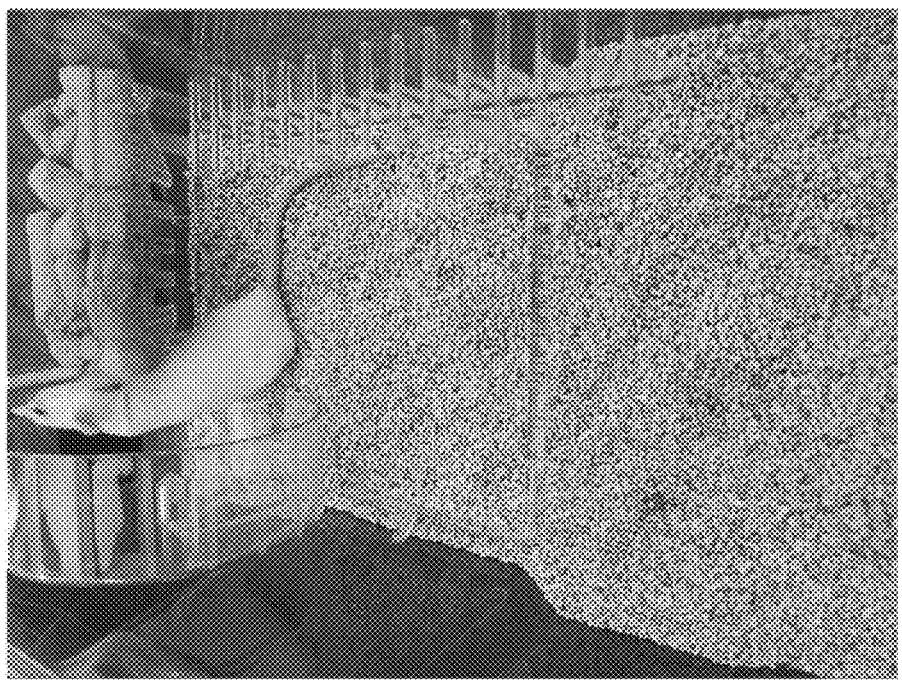
Figure 6A:
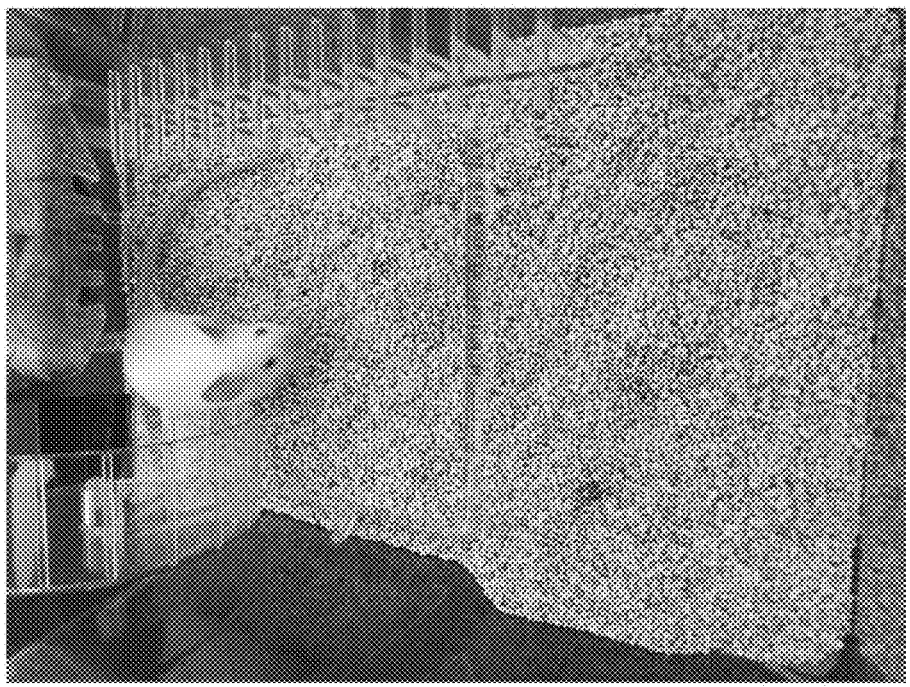

As in step 420, a visible light image of the experimental animal may be captured with visible light camera 134. The visible light image may be captured through the side of cage 100, for example through a window 120 as described above and depicted in FIG. 3B. In other embodiments, the visible image may be captured from above, for example from a visible light camera 134 mounted within electronic monitor 200, as depicted in FIG. 8. While it may be advantageous for visible light camera 134 and infrared camera 132 to capture images from the same, adjacent (e.g., as shown in FIGS. 3B and 8), and/or or otherwise similar vantage points, embodiments where the cameras are located in disparate locations are also contemplated. FIGS. 5A, 6A, and 7A each provide an illustrative visible light image of an experimental animal in a cage taken from above, which correspond to FIGS. 5B, 6B, and 7B, respectively. While FIGS. 5B, 6B, and 7B each illustrate a zoomed-in or cropped infrared image, it is contemplated the infrared image may depict a substantially larger portion of the cage, such as the subject matter shown in FIGS. 5A, 6A, and 7A or the like. Further, it may be noted that the infrared image of FIG. 7B has been adjusted to be at the same scale and rotation as the visible light image as FIG. 7A for illustrative purposes.

In some embodiments, the visible light image may be a visible light video comprising multiple frames captured in sequence and/or the infrared image may be an infrared video comprising multiple frames captured in sequence. In other embodiments, the visible light image may be a single frame of or a combination of multiple frames of a visible light video and/or the infrared image may be a single frame of or a combination of multiple frames of an infrared video.

In exemplary embodiments, the visible light and infrared images may be captured substantially simultaneously, for example, within 0.25 seconds, 0.1 seconds, or even 0.05 seconds of each other. In other embodiments, step 420 may occur prior to step 210. Further, in embodiments where videos are captured, a visible light video and an infrared video may be captured substantially simultaneously.

As in step 450, the position of at least one part of the experimental animal may be determined. Computer vision processing techniques techniques to identify an object, such as experimental animal, and as well as specific parts of the animal are well known in the art. An experimental animal may be identified within an image through a segmentation process, whereby an image is divided into various portions to identify a target object relative to a background, other stationary object, and/or other moving object, even when the lighting may be dynamic. For example, Branson, K. et al. Tracking Multiple Mouse Contours (Without Too Many Samples). 2005 *IEEE Computer Society Conference on Computer Vision and Pattern Recognition* (CVPR '05), incorporated herein by reference in its entirety, teaches a method of identifying an experimental animal, even where multiple animals overlap in the same image. As another example example, Stauffer, C., and W. E. L. Grimson. "Adaptive Background Mixture Models for Real-time Tracking." *Proceedings*. 1999 *IEEE Computer Society Conference on Computer Vision and Pattern Recognition* (Cat. No PR00149), incorporated herein by reference in its entirety, describes a method of segmentation. Additionally, Dalal, N., and B. Triggs. "Histograms of Oriented Gradients for Human Detection." 2005 *IEEE Computer Society Conference on Computer Vision and Pattern Recognition* (CVPR '05), incorporated herein by reference in its entirety, describes a method of object recognition based on histograms that recognizes an object in various positions; although the references uses humans as an example, such method may easily be adapted to recognize experimental animals in various positions.

The determination of coordinates for parts of an object within an image, such as coordinates for an experimental animal's eyes, ears, tail, and paws, are also well known in the art. For example, Viola, P. and Jones, M. "Robust Real-time Object Detection," *Cambridge Research Laboratory Technical Support Series*, CRL2001/01, February 2001 (available at http://www.hpl.hp.com/techreports/Compaq-DEC/CRL-2001-1.pdf), incorporated herein by reference in its entirety, utilizes an integral image and a learning algorithm to quickly detect eyes as a key component of facial recognition in humans; this may easily be adapted to detect eyes in images of experimental animals, such as mice. As used herein "eye" refers to the actual eye of an animal, but may also refer to the general region of the eye, including the eye socket, as well as other areas around the eye that are similar in temperature.

Figure 7C:
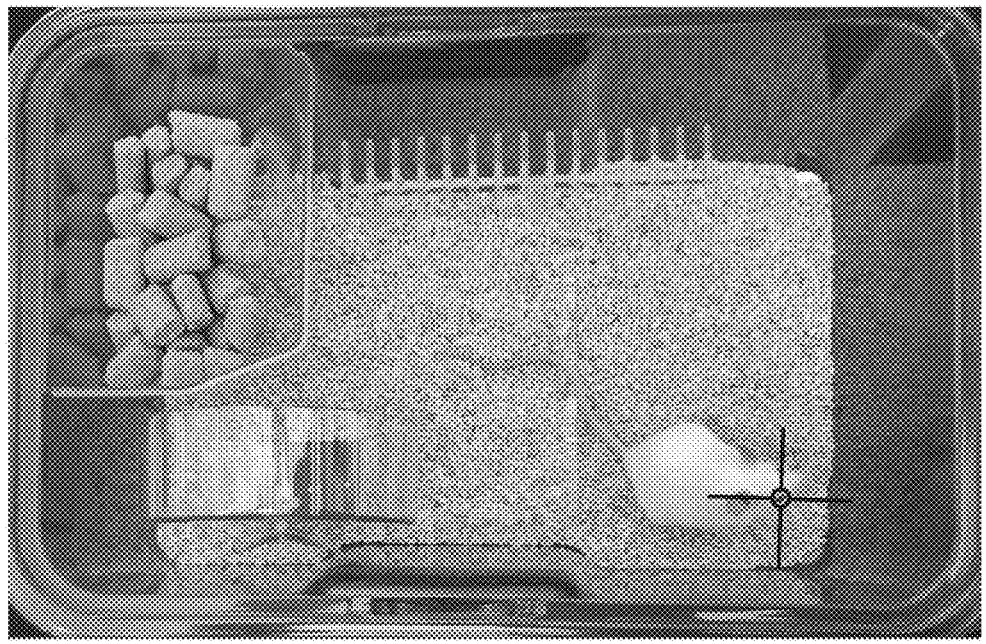
Figure 7D:
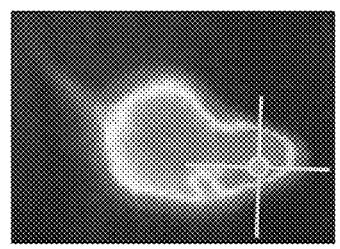
Figure 7E:
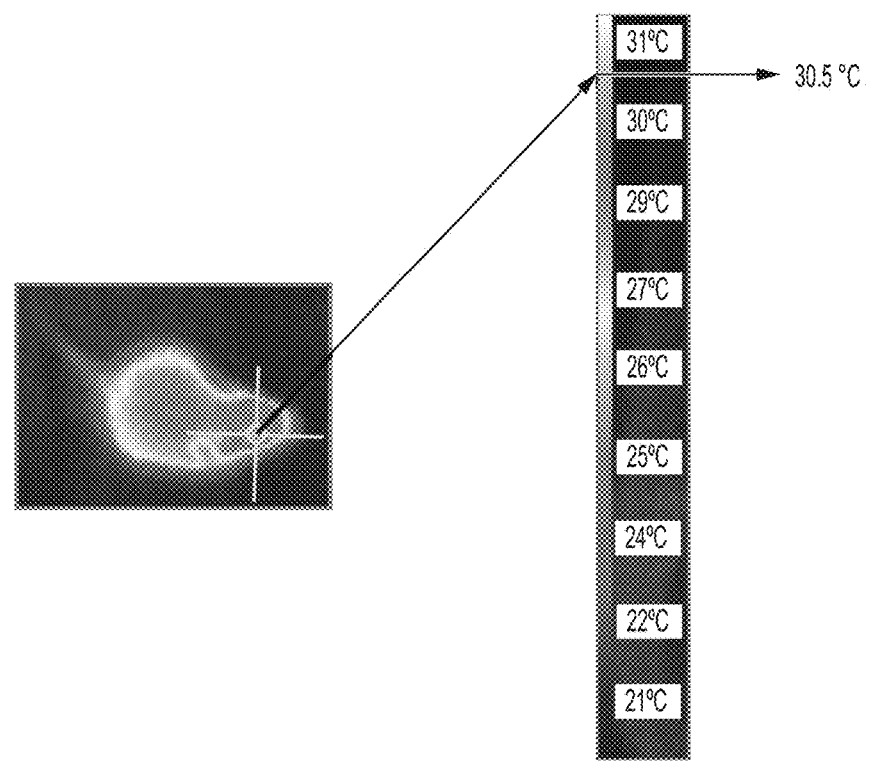
Figure 7F:
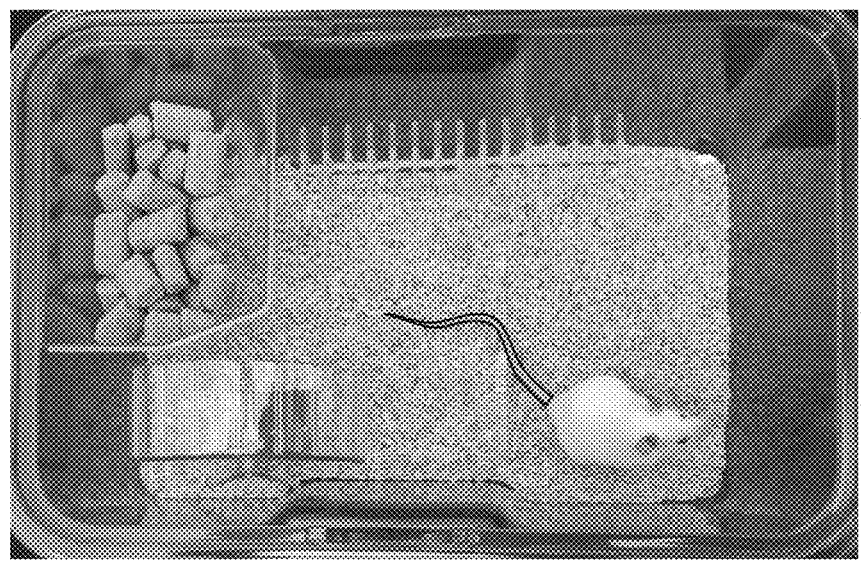

Additionally, the eyes of a mouse, or another experimental animal, have a set, predictable position with respect to other features of the mouse, such as the ears and nose. Identification of all of such features may be made or confirmed based on their coloring (e.g., the ears and nose may have a pinkish hue), darkness, shape, size, and/or proximity or orientation vis-à-vis the other features. Similarly a tail may be identified by its color; its position with respect to the identified experimental animal (e.g., at the end of the body); and/or its curved or winding shape, using, for example, the method histogram-based or machine learning methods of Dalal and Viola referenced above. And, as may be visible from images taken from the side of cage 100, paws may be identified by color; their position with respect to the identified experimental animal; and/or their particular shape, using, for example, the histogram-based or machine learning methods of Dalal and Viola referenced above. Ohayon, S. et al. (2013). Automated Multi-day Tracking of Marked Mice for the Analysis of Social Behaviour. Journal of Neuroscience Methods, 219(1), 10-19, incorporated herein by reference in their entireties, provide additional examples of body, head and tail identification, including where markers are use. As examples, FIGS. 7C and 7F depict, respectively, the identification of an eye and a tail of an experimental animal.

The location of additional parts of an animal, for example, stereotypical locations for brown adipose tissue deposits such as the interscapular area, or a tumor that is injected or grown, may be determined by reference to other identified parts. For example, coordinates for a brown adipose tissue deposit located in the interscapular area may be determined by extrapolating a predicted location from the positions of the ears, eyes, and/or other more easily identifiable parts. Similarly, coordinates for a known tumor may determined by extrapolating a predicted location from the positions of the base of the tail, ears, eyes, and/or other parts.

Additionally, or alternatively, the infrared image may be used in identifying the experimental animal and its various parts. For example, as can be readily observed from FIGS. 5B, 6B, and 7B, substantially the outline of the body of a mouse and the outline of the mouse's ears may have as similar temperature, for example approximately 27-29° C., which is typically elevated temperature when compared to the temperature of the background. The ears, nose, and base of tail may indicate a lower temperature, for example approximately 24-27° C. The eyes are likely to indicate the highest temperature on the animal, for example approximately 29-34° C. The paws may have a temperature of approximately 22-36° C.

The coordinates may reference the position of at least one part of the experimental animal in the visible light image, in the infrared image, and/or in a plane corresponding to a surface of the cage 100, for example the cage floor 115 or wall 110, depending on the location of cameras 132, 134. The coordinates may define an area of interest that corresponds to a plurality of pixels in the infrared image. Where both a visible light image and an infrared image are used to determine part position, the images may be correlated with one another, as in step 455, discussed below, during or prior to this positioning determining step. That is, corresponding portions or elements of each image are mapped to one another.

If the identification of a particular part is sought and the part is not found such that no coordinates may be determined, the process may start again such that a more suitable set of images may be captured. For example, if identification of an eye of an experimental animal is sought and the animal is facing directly away from the camera(s) at the time of image capture, the eye may be absent from the image(s) and therefore it may not be possible to reliably determine the position of the eye.

In some embodiments, a distance of an experimental animal or its parts from visible light camera 134 and/or infrared camera 132 may be determined, for example, by comparing the area occupied by experimental animal within the image(s) to a predetermined area representative of the actual size of the animal. That is, the larger the area occupied by experimental animal is with respect to the predetermined area, the closer the animal may be to the camera(s). In some embodiments, the distance may be estimated by taking a ratio these values and cross-referencing a lookup table or the like.

In some embodiments, angles of identified parts of the experimental animal with reference to visible light camera 134 and/or infrared camera 132 may also be determined. First, a pose of the experimental animal in the cage may be determined via methods well known in the art. For example, Wang, Chun-Kai. Multiple mice tracking using Microsoft Kinect. Diss. Massachusetts Institute of Technology, 2013 (available at http://hdl.handle.net/1721.1/85517), incorporated herein by reference in its entirety, utilizes a statistical shape model and shape tracking to estimate the pose of a mouse. As another example, Xu, C. et al. "Estimate Hand Poses Efficiently from Single Depth Images." *International Journal of Computer Vision Int J Comput Vis* 116.1 (2015): 21-45, incorporated herein by reference in its entirety, discusses various methods by which poses of human hand gestures may be estimated; these methods may easily be adapted to detect the simpler poses of experimental animals. Then, once the experimental animal's pose is determined, the angle of the part of interest may be estimated based on an anatomy model of the experimental animal. For example, if the camera(s) capture images though a wall 110 and if the animal's pose is such that its head is pointed towards at a corner of the cage, a lookup table may be used to approximate the angle of the eyes of the experimental animal with respect to the camera(s). Indeed, well known methods for object detection are frequently applied to estimating the articulated pose of non-rigid objects by simply learning many "part detectors" (e.g., face, ear, hand, foot, elbow, shoulder) and fusing the results with a object-specific geometric model (e.g., skeleton or constellation model). For example, Bourdev, L et al. "Poselets: Body part detectors trained using 3d human pose annotations." 2009 *IEEE 12th International Conference on Computer Vision*. IEEE, 2009 and Felzenszwalb, P. F., et al. "Object detection with discriminatively trained part-based models." *IEEE transactions on pattern analysis and machine intelligence* 32.9 (2010): 1627-1645, incorporated herein by reference in their entireties, provide examples of such techniques.

Controller 140 may process the visible light image(s), the infrared image(s), both, and/or other data to identify the experimental animal in a cage, identify one or more parts of the animal, and/or estimate their respective positions, including distance and angle with respect to the camera(s).

As in step 455, the visible light image and an infrared image may be correlated with one another. That is, corresponding portions or elements of each image may be mapped to one another and/or both may be mapped to a plane corresponding to a surface of the cage 100. Where visible light camera 134 and infrared camera 132 to capture images from the same, adjacent, or otherwise similar vantage points, the trigonometric mathematical computations needed for the correlation step may be simplified or omitted altogether. In some embodiments, controller 320 may use homography to project the visible light image and the infrared image onto a plane corresponding to the cage floor or wall 110 opposite the camera(s) to correlate the images. For example, the projected views may be fused into a synthetic overhead view of the cage floor 115 or synthetic side view of wall 110, where one or both cameras 132, 134 chosen for certain pixel information in the synthetic view are selected to reduce occlusions and maximize sensing resolution. Controller 140 may accomplish the correlation step.

As in step 460, the temperature of the at least one identified part of the animal may be determined. To accomplish this, pixels of the infrared image corresponding to the coordinates of the at least one identified part may be assessed. The color of each pixel represents an observed temperature for that pixel. An overall observed temperature of a part may be determined through evaluation of pixels corresponding to that part. In various embodiments, an average of all pixel values corresponding to the coordinates, an average of all pixel values after outlier values are omitted, all pixel values corresponding to a central portion of the coordinates, a weighted average focused on the center portion of the coordinates, and/or the like may be used to determine an overall observed temperature for the part. For example, FIG. 7D illustrates how pixels of an infrared image corresponding to the coordinates of an eye may be assessed. In this example, as shown in FIG. 7E, an average of all pixel values corresponding to the coordinates of the eye provides that the overall observed temperature of the eye is 30.5° C.

Figure 7G:
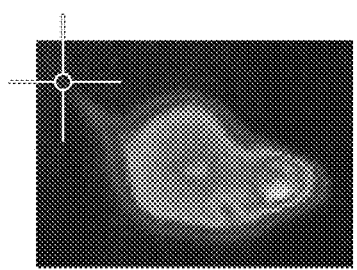

In another example, FIG. 7G illustrates how pixels of an infrared image corresponding to the coordinates of a tail may be assessed. In this example, all pixel values corresponding to a central portion of the coordinates may be used to determine an overall observed temperature for the tail.

In some embodiments, the temperature values corresponding to the various pixel colors may be calibrated, for example using a thermal reference 150. This may be advantageous where, for example, the accuracy of infrared camera 132 may potentially be less than desirable. Further, use of a thermal reference 150 may permit use of more economical infrared cameras 132 that may otherwise be unsuitable due to their unreliable accuracy. A thermal reference 150, for example as shown in FIG. 8, may maintain a constant temperature within a high degree of accuracy. For example, thermal reference 150 may comprise a simple heater, a thermostat, and a small metal block coated with a material of known emissivity. In some embodiments, the emissivity may be similar to that of mouse skin or another experimental animal. Additionally, the ambient temperature of a cage, for example, as may be measured by air inlet and/or air outlet temperature sensors, may provide a proxy temperature reference indicative of the temperature of the bedding within cage 100. Thus, the bedding may be a ubiquitously visible reference for the cold end of the thermal spectrum. An infrared image may capture observed temperatures for the bedding and/or thermal reference 150. By associating the pixels representing thermal reference 150 with the constant accurate temperature of thermal reference 150 and/or by associating the pixels representing the bedding with the proxy thermal reference temperature, the pixel-temperature scale may be calibrated. While at least one thermal reference may be used to compensate for offset error (aka zero error), at least two thermal references may be needed to compensate for gain error (aka span error).

Further, it may be advantageous to adjust the overall observed temperature of a part to compensate for the angle and distance of the part with respect to the infrared camera 132. This is because where a part is far from infrared camera 132 and/or does not directly face infrared camera 132, the overall observed temperature of the part might not accurately reflect that part's temperature. For example, in FIG. 6B, where the eyes of the mouse are substantially directly facing infrared camera 132 and an average of all pixel values corresponding to the coordinates are used to determine the overall observed temperature, the overall observed temperature of each eye is approximately 33° C.; this is because many more pixels are able to capture the "pure" temperature of the eyes relative to pixels reflecting temperatures of areas adjacent to the eye, resulting in a more accurate observed overall temperature. By contrast, in FIGS. 7B, 7D, and 7E, where the eye of the same mouse is substantially oblique to infrared camera 132 and the overall observed temperature is determined the same way, the overall observed temperature of the eyes is approximately 30.5° C.; this is because fewer pixels are able to capture the "pure" temperature of the eyes and relatively more pixels reflect temperatures of areas adjacent to the eye are included in the average, resulting in a less accurate observed overall temperature. Similarly, where an animal is further away, each part may be represented by fewer pixels, which may result in a less accurate observed overall temperature.

To adjust the overall observed temperature of a part to compensate for the angle and distance of the part with respect to the infrared camera 132, distance and angle may first be estimated as discussed above. Then, an appropriate adjustment to the overall observed temperature may be determined by using a lookup table indexed by angle and/or distance, or the like. Such a lookup table may be experimentally created by capturing infrared images of the same part of the same experimental animal from a variety of angles and/or distances with infrared camera 132 and deriving an appropriate adjustment for a plurality of suitable angles and/or distance combinations. The lookup table may be created such that an adjusted final part temperature approximates the overall observed temperature of the part from close-up distance and/or direct infrared image capture.

Additionally, or alternatively, the distance and/or angle with respect to infrared camera 132 may be used to determine that a particular infrared image is not suitable for determining a temperature. That is, an angle may be determined to be so oblique or a distance may be determined to be so large that an accurate part temperature cannot be determined with sufficient accuracy, even with adjustment as described above. For example, the second eye of the experimental animal depicted in FIGS. 7A and 7B (which is not the eye assessed in FIG. 7E), is practically indistinguishable from the outline of the animal's body in the infrared image of FIG. 7B. Here, the eye is positioned so obliquely to the infrared camera 132 that its temperature may not be measured with reasonable accuracy. In such a circumstance, it may be desirable to repeat steps 410, 420, and 450, so that a more suitable infrared image may be used. Such a technique may prevent or reduce the likelihood of inaccurate temperature measurements.

As in step 470, that least one physiological characteristic of the animal may be determined.

As one example of determining a physiological characteristic, the core temperature of an experimental animal may be determined. To determine this, a part temperature of an eye of may be obtained. The part temperature of the eye may have been adjusted for angle and/or distance as discussed with respect to step 460. Then, a core temperature of the experimental animal may be determined by using a lookup table indexed by the eye temperature or the like. Alternatively, other parts of an experimental animal, for example, exposed skin of a partially shaved or otherwise hairless rodent may be used.

Such a lookup table may be empirically built by manually taking the temperature of an experimental animal, for example using a rectal probe, proximal in time with capturing an infrared image of the eye of the same experimental animal. The process may be repeated at least until enough disparate data points are gathered such that a core temperature/eye temperature relationship curve may be estimated. In some embodiments, for example where a core temperature/eye temperature relationship curve is sought for a set of experimental animal clones, proximal in time may mean within seconds or minutes. However, in other embodiments, for example, where the core temperature/eye temperature relationship curve is to be adjusted or confirmed for a specific experimental animal, proximal in time may mean within longer time ranges, such as the same day.

As another example of determining a physiological characteristic, a presence or degree of swelling or inflammation may be determined. For example, data from an infrared image of the paw of an experimental animal can provide a reliable indicator of the magnitude of paw edema. This is because certain paw surface temperatures may vary in concert with the level of swelling or inflammation in a particular region of interest. In turn, a measure of swelling or inflammation may be a reliable indicator of experimentally induced arthritis. Sanchez, B. M. et al. (2008). "Use of a portable thermal imaging unit as a rapid, quantitative method of evaluating inflammation and experimental arthritis." *Journal of Pharmacological and Toxicological Methods*, 57(3), 169-175, and Jasemian, Y. (2011). "Refinement of the Collagen Induced Arthritis Model in Rats by Infrared Thermography." *BJMMR British Journal of Medicine and Medical Research*, 1(4), 469-477), both of which are incorporated herein by reference in their entireties, provide examples of well known techniques for measuring swelling, inflammation, and arthritis by evaluating data from infrared images.

Where an infrared image is captured from above, for example from an infrared camera 132 within electronic monitor 200, it may be difficult or impossible to assess paw temperature from a resulting image because the paws are likely to be hidden. However, where an infrared image is captured from the side, for example through window 120 in wall 110, the paws of an animal may be viewed from this side. A given level of paw swelling may manifest in different observed paw temperatures when an infrared image captures the paw from the side as opposed to a head-on view. Thus, where paw temperatures are only available from a side view, it may be necessary to use an empirically determined lookup table or the like to map side-view-observed paw temperatures to corresponding degrees of swelling or inflammation. Further, unwanted variances in observed paw temperature may be reduced by using a reference temperature of the experimental animal and accordingly adjusting the paw temperature or the like. The experimental animal's eye temperature or derived core temperature may be used as such a reference temperature of the experimental animal instead of or in addition to using a temperature observed from a shaved or bald patch of the skin of the experimental animal, as suggested in the Jasemian reference.

As yet another example of determining a physiological characteristic, a degree of brown adipose tissue (aka brown fat) thermogenesis may be determined. Rodents may typically include brown adipose tissue deposits in the interscapular area, e.g. just behind their ears and between their shoulder blades. Thermogenesis of such brown adipose tissue deposits may be assessed by evaluating the temperature of skin adjacent to such deposits. Such temperature evaluation may be accomplished through use of infrared images to arrive at an observed part temperature, and a degree of thermogenesis may be derived through the use empirically determined lookup table or the like. Al-Noori, S. et al. "Brown Adipose Tissue Thermogenesis Does Not Explain the Intra-administration Hyperthermic Sign-reversal Induced by Serial Administrations of 60% Nitrous Oxide to Rats." *Journal of Thermal Biology* 60 (2016): 195-203, and Smriga, M. et al. "Use of Thermal Photography to Explore the Age-dependent Effect of Monosodium Glutamate, NaCl and Glucose on Brown Adipose Tissue Thermogenesis." *Physiology & Behavior* 71.3-4 (2000): 403-07, both of which are incorporated herein by reference in their entireties, provide examples of assessing brown adipose thermogenesis from temperature data derived from infrared images.

It may be advantageous to provide experimental animals with a hairless interscapular region, which may be obtained by shaving or depilation in some embodiments or by providing a hairless experimental animal, to improve accuracy of temperature measurements. Further, unwanted variances in observed tumor temperature may be reduced by using a reference temperature of the experimental animal and accordingly adjusting the paw temperature or the like. The experimental animal's eye temperature or derived core temperature may be used as such a reference temperature of the experimental animal instead of or in addition to using a temperature observed from a shaved or bald patch of skin.

As yet another example of determining a physiological characteristic, a degree of tumor vascularization may be determined. Tumor vascularization may be illustrative of tumor development, and measurement of superficial temperatures above the tumor may provide an indirect measure of tumor vascularization. This is discussed in Faustino-Rocha, A. I. et al. "Ultrasonographic, Thermographic and Histologic Evaluation of MNU-induced Mammary Tumors in Female Sprague-Dawley Rats." *Biomedicine & Pharmacotherapy* 67.8 (2013): 771-76 and Poljak-Blazi, M. et al. "Specific Thermographic Changes During Walker 256 Carcinoma Development: Differential Infrared Imaging of Tumour, Inflammation and Haematoma." *Cancer Detection and Prevention* 32.5-6 (2009): 431-36, both of which are incorporated herein by reference in their entireties.

A tumor may be grown in a location or part of an experimental animal that may be readily viewable, for example, in an area just above the base of the tail, in a leg, or on the top of the head, and located using the computer vision techniques disclosed above. A degree of tumor vascularization may be determined by evaluating the temperature of skin observed at the tumor location, with higher temperatures being associated with more vascularization and lower temperatures being associated with less vascularization. Such temperature evaluation may be accomplished through use of infrared images to arrive at an observed part temperature, and a degree of tumor vascularization may be derived through the use empirically determined lookup table or the like.

It may be advantageous to provide experimental animals with a hairless tumor region, which may be obtained by shaving or depilation of the skin covering the tumor in some embodiments or by providing a hairless experimental animal, to improve accuracy of temperature measurements. Further, unwanted variances in observed tumor temperature may be reduced by using a reference temperature of the experimental animal and accordingly adjusting the observed tumor temperature or the like. The experimental animal's eye temperature or derived core temperature may be used as such a reference temperature of the experimental animal instead of or in addition to using a temperature observed from a shaved or bald patch of skin.

As yet another example of determining a physiological characteristic, a degree of hair loss (e.g., alopecia) may be determined, as well as the locations of such hair loss. In one example, the outline of the experimental animal may be determined based on the visible light and/or infrared images. Within this outline, areas of hair loss may be determined by quantifying areas of elevated temperature within the experimental animal outline in the infrared image. Thus, it may not be necessary to determine the positions of individual parts of the experimental animal in some embodiments. A degree of hair loss may be determined by, for example, calculating what portion of the experimental animal has a raised temperature; the calculation may account for the fact that certain portions of an experimental animal, for example the eyes and paws, are likely to have an elevated surface temperature without being indicative of hair loss. In other embodiments, the outline may be processed to ensure that the eyes, paws, and/or other parts known to have elevated temperatures are excised from the outline before calculation. In yet other embodiments, a specific area of hair loss may be found, and then its size and/or position subsequently identified.

Figure 9:
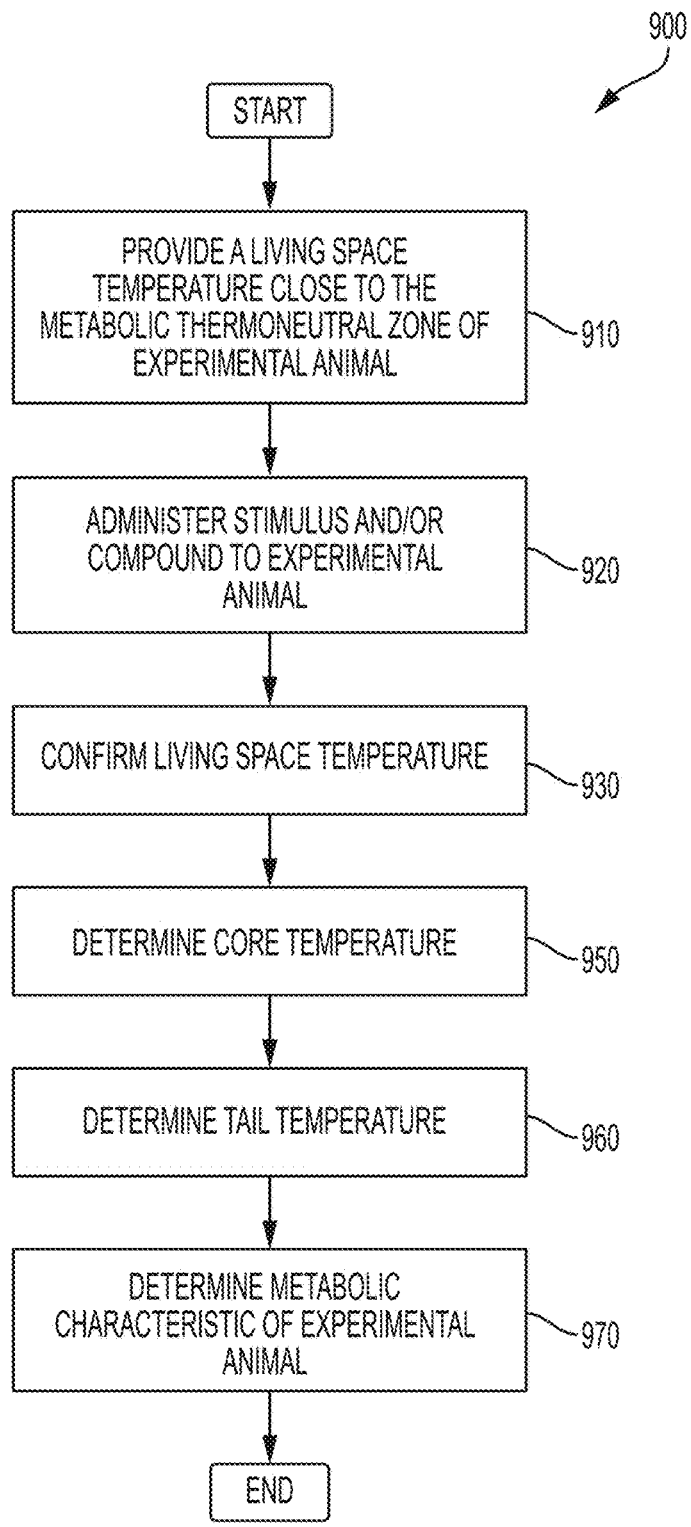
FIG. 9 is a flowchart of an example of a method of determining at least one metabolic characteristic of an experimental animal.

FIG. 9 is a flowchart of an exemplary embodiment of determining at least one metabolic characteristic of an experimental animal in a living space. As discussed in Gordon, C. J. (1993). *Temperature Regulation in Laboratory Rodents*. Cambridge: Cambridge University Press, which is incorporated herein by reference in its entirety, a metabolic thermoneutral zone (TNZ) may be understood as a range of ambient temperatures at which an animal's metabolic rate generally is at its lowest and at which regulatory changes in metabolic heat production or evaporative heat loss are generally not needed. A TNZ may be bound at a lower end with a lower critical ambient temperature, below which an animal will generally increase heat production. And, a TNZ may be bound at an upper end at an upper critical ambient temperature, above which the animal's metabolic rate increases above basal levels and evaporative heat loss-mechanisms of the animal might activate.

As in step 910, the living space may be provided with a temperature near or within the TNZ of the experimental animal being studied. As examples, the TNZ for various strains of mice, from lower critical ambient temperature to upper critical ambient temperature, may be 30.6° C. to approximately 34° C., 26° C. to 30° C., or 31° C. to 34° C. The TNZ for various strains of gerbils may be 30° C. to 35° C., 30° C. to 39° C., 28° C. to 32° C., or 32° C. to 34° C. The TNZ for various strains of rats may be may be 29.2° C. to 31.0° C., 30° C. to 33° C., 28° C. to around 33° C., 28° C. to 32° C., 28° C. to 34° C., 22° C. to 27° C., or around 26.5° C.

In exemplary embodiments, the living space temperature to be provided may be within a predefined range that is near or within the metabolic thermoneutral zone (TNZ) of the experimental animal. In various examples, this predefined range may include only temperatures that are within the metabolic thermoneutral zone of the animal or are within 2° C., 1° C. or 0.1° C. of the TNZ of the experimental animal. In other examples, the predefined range may include only temperatures that are within 2° C., 1° C., or 0.5° C. of the lower critical ambient temperatures of the TNZ of the experimental animal. In yet other examples, the predefined range may be about 27° C. to about 28° C., 28° C. to about 29° C., or 29° C. to about 30° C. In yet other embodiments, the predefined range may be entirely above the upper critical ambient temperature, but within 5° C., 4° C., 3° C., 2° C., or 1° C. of it. In yet other embodiments, the predefined range may be entirely below the lower critical ambient temperature, but within 5° C., 4° C., 3° C., 2° C., or 1° C. of it.

As vivariums are generally kept cooler than a given experimental animals' TNZ, a desired living space temperature may be provided by a heater or heating element, for example, within cage 100 or electronic monitor 200 that operates in conjunction with a thermostat. Air conditioning or another cooling apparatus may optionally be included if the temperature becomes too warm. In other embodiments, air at the desired living space temperature may be vented in. Although a smaller predefined range of temperatures may provide more accurate experimental data than a wider range or predefined temperatures, as ranges get smaller it may become more difficult or require more expensive equipment and maintenance to sustain a living space temperature within the predefined range.

As in step 920, a chemical compound and/or other stimulus may be provided to the experimental animal. Such compound may include a pharmaceutical, a possible or putative pharmaceuticals, prototypes of pharmaceuticals, or compounds intended to affect mechanisms similar to what related pharmaceuticals might affect. The stimulus may be social, physical, relating to nutrition, relating to odor, relating to mating, relating to hydration, and/or the like. Because, in exemplary embodiments, the experimental animal's metabolism is to be checked in later steps, this optional step is included in the flowchart to provide an example of when a chemical and/or stimulus might be provided in order to assess the metabolic affect of such chemical and/or stimulus. For example, pharmaceuticals that increase metabolism are generally desired to promote weight loss; compound candidates for such drugs may be assessed via this method.

As in step 930, the living space temperature is confirmed. In some embodiments, the ambient temperature of a cage, for example, may be measured and confirmed by air inlet and/or air outlet temperature sensors. In other embodiments, the cage may include a digital thermometer, whose output is provided to controller 140, or an uncoupled thermometer that may be captured in a visible light image and read when the image is processed. In some embodiments, an infrared image of the experimental animal, animal bedding, and a thermal reference 150 with a temperature within the predefined range may be captured with infrared camera 132. Here, the living space temperature may be confirmed by comparing the color of the thermal reference 150 to the color of the bedding in the infrared image. With reference to the calibration discussion above, the bedding may be a ubiquitously visible reference for temperature of the cage. Multiple thermal references 150 at various temperatures may be provided in cage 100 for calibration purposes, as discussed above, or to visually establish the predefined range in the infrared image. In yet other embodiments, step 930 may not be a step distinct from step 910. For example, proper operation of a thermostat may serve as confirmation that the living space temperature is within the predefined range.

As in step 950, the core temperature of the experimental animal may be determined. The core temperature may be determined based on the observed temperature of an eye of the experimental animal in an infrared image, as discussed above. In step 950, an infrared image, perhaps along with a visible light image, may be captured if it was not already captured during step 930. In other embodiments, the core temperature of the animal may be determined by assessing the color of a portion of hairless skin that is included in an infrared image. Or, the core temperature may be manually taken with a thermometer. In yet other embodiments, as discussed below, this step may be excluded entirely. That is, especially where the temperature of the living space is confirmed, the core temperature of the experimental animal may be assumed to be normal or near normal.

As in step 960, the tail temperature of the experimental animal may be determined. As described above, such temperature may be determined by processing of an infrared image of the animal, and, in some embodiments a visible light image. In step 960, an infrared image, perhaps along with a visible light image, may be captured if it was not already captured during either of steps 930 and 950. Alternatively or additionally to determining the tail temperature, a paw or foot temperature may be determined.

As in step 970, a metabolic characteristic of the experimental animal may be determined. Mice, rats, and other rodents control heat loss through adjustments in vasomotor tone (PVMT) of, for example, their tails or feet. For example, at typical room temperature (e.g., 20° C.-25° C.) or when a mouse is cold, blood flow through the tail of the mouse is restricted to prevent heat loss. In such circumstances, the temperature of the tail of the mouse may be, for example, 15° C.-25° C., measurably lower than its core temperature. However, when the mouse is too warm the tail is vasodilated to allow blood to flow through the tail at higher rates, and subsequently dissipate heat through the substantially hairless tail surface. In such circumstances, the temperature of the tail of the mouse may approach or even meet its core temperature. Thus, PVMT and consequently a metabolic rate of an experimental animal may be indicated by the experimental animal's tail temperature.

Notably, different portions of the tail may be at different temperatures at any given instant. For example, because some heat dissipates from the flowing blood by the time it reaches the tip of the tail, the tip of the tail is likely to be cooler than the base of the tail. Thus, more precise data may be gathered by consistently taking the tail temperature from the same portion or portions of the tail. For example, the tail temperature may be an average of all tail temperatures, all tail temperatures but outliers, the tip section of the tail, the middle section of the tail, the base section of the tail, and/or the like.

In one embodiment, a determination of metabolic rate increase and/or of metabolic rate may be determined by taking the difference (aka delta) between the experimental animal's core temperature and its tail temperature. If the animal's metabolic rate is normal, the difference may be expected to be at its maximum. The difference between the core and tail temperatures will become smaller and smaller as the metabolism of the animal increases. Then, a metabolic rate may be determined by using a lookup table indexed by difference between the core and tail temperatures, and perhaps the ambient temperature of the living space, or the like. Such a lookup table may be empirically created by measuring the metabolic rate of the animal and simultaneously or near simultaneously obtaining tail, core, and/or ambient temperatures, for example via an infrared image capture.

In this embodiment, it may not be necessary to maintain and/or confirm a predetermined temperature range as in steps 910 and 930. For example, the living space temperature may be permitted to stay at or near room temperature. Here, because the animal's core temperature is included as part of the metabolic characteristic determination calculation, any measured increase in metabolic is activity is likely to be accurate. However, by providing a living space temperature at or around the experimental animal's TNZ, especially near its lower critical ambient temperature, a modest increase in metabolism is more likely to result in an measurably increased tail temperature and increases in tail temperatures are likely to occur more rapidly.

In another embodiment, step 950 may be omitted and a normal core temperature may be assumed. Here, a metabolic rate may be determined by using a lookup table indexed by tail temperature, and perhaps the ambient temperature of the living space, or the like. Such a lookup table may be empirically created by measuring the metabolic rate of the animal and simultaneously or near simultaneously obtaining tail and/or ambient temperatures, for example via an infrared image capture.

It is contemplated that portions of the metabolic characteristic determining process (e.g., steps 930, 950, 960, and 970) may be continuously repeated after the compound and/or stimulus is administered to determine how long a metabolic response of the experimental animal takes to begin, how long it takes to finish, and/or the manner in which it progresses. Such a technique may deliver richer datasets.

It is contemplated further that, for some studies, the metabolic characteristic determining process may be repeated multiple times at a plurality of predefined temperatures in and around the TNZ of the animal. Such serial measurements may provide more robust datasets from which the metabolic effects of particular compounds and/or stimuli may be more thoroughly evaluated.

Alternatively or additionally to determining a metabolic characteristic based on the tail temperature, a paw or foot temperature may be used in a similar fashion.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the appended claims. It is also to be understood that the terminology used herein is for the purpose of describing particular aspects only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order that is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein.

In this specification, various embodiments have been described with reference to the accompanying drawings. It will be apparent, however, that various other modifications and changes may be made thereto and additional embodiments may be implemented without departing from the broader scope of the claims that follow. The specification and drawings are accordingly to be regarded in an illustrative rather than restrictive sense.

We claim:

1. A method for determining at least one physiological characteristic of at least one experimental animal in a cage, the method comprising:

capturing at least one infrared image of at least one experimental animal in a band of infrared radiation that is within the range of from about 3 μm to about 14 μm in wavelength;

capturing at least one visible image of the at least one experimental animal;

correlating the at least one infrared image and the at least one visible light image; and determining the at least one physiological characteristic of the at least one experimental animal based at least in part on the correlation.

2. The method of claim 1, wherein:

capturing at least one infrared image comprises capturing multiple video frames that depict temperatures of the at least one experimental animal; and capturing at least one visible image of the at least one experimental animal comprises capturing multiple video frames that depict visible light.

3. The method of claim 1, wherein the at least one experimental animal comprises a rodent.

4. The method of claim 1, wherein capturing the at least one infrared image and capturing the at least one visible image occur within 0.1 seconds of each other.

5. The method of claim 1, wherein correlating the at least one infrared image and the at least one visible light image further comprises:

determining a position of at least one part of the at least one experimental animal in the at least one visible light image; and determining a part temperature of the at least one part of the at least one experimental animal based on data from the at least one infrared image.

6. The method of claim 1, wherein determining the at least one physiological characteristic comprises assessing a degree of hair loss of the at least one experimental animal.

7. The method of claim 5, wherein determining the at least one physiological characteristic comprises assessing a degree of tumor vascularization at the at least one part of the at least one experimental animal.

8. The method of claim 5, wherein determining the at least one physiological characteristic comprises assessing a degree of brown adipose tissue thermogenesis occurrence at the at least one part of the at least one experimental animal.

9. The method of claim 5, wherein determining the at least one physiological characteristic comprises determining a core temperature of the at least one experimental animal.

10. The method of claim 5, wherein determining the part temperature further comprises using a thermal reference captured in the at least one infrared image to calibrate a temperature scale of the at least one infrared image.

11. The method of claim 5, wherein determining the part temperature further comprises adjusting a temperature provided in the at least one infrared image based on at least one of a distance of the position from a camera that captured at least one infrared image and an angle of the at least one part of the experimental animal with respect to the camera.

12. An apparatus to determine at least one physiological characteristic of at least one experimental animal, the apparatus comprising:

a cage housing at least one experimental animal, the cage comprising at least one wall with a window that is transparent to a band of infrared radiation that is within the range of from about 3 μm to about 14 μm in wavelength;

a first image capture device configured to capture at least one infrared image of the at least one experimental animal through the transparent window;

a second image capture device configured to capture at least one visible light image of the at least one experimental animal; and a controller configured to:

receive the at least one infrared image, receive the at least one visible light image, and determine the at least one physiological characteristic of the at least one experimental animal based on the at least one infrared image and the at least one visible light image.

13. The apparatus of claim 12, wherein the second image capture device is further configured to capture the at least one visible light image through the transparent window.

14. The apparatus of claim 12, wherein the transparent window comprises NaCl.

15. The apparatus of claim 14, wherein the transparent window consists essentially of NaCl.

16. The apparatus of claim 12, wherein:

the at least one visible light image comprises multiple video frames that depict captured visible light; and the at least one infrared image comprises multiple video frames that depict temperatures of the at least one experimental animal.

17. The apparatus of claim 12, wherein the controller is further configured to:

determine a position of at least one part of the at least one experimental animal using the at least one visible light image; and use at least the data from the at least one infrared image and the determined position of the at least one part of the at least one experimental animal, to determine at least one physiological characteristic of the at least one experimental animal.

18. The apparatus of claim 17, wherein the at least one physiological characteristic comprises a degree of hair presence.

19. The apparatus of claim 17, wherein the at least one physiological characteristic comprises a degree of tumor vascularization.

20. The apparatus of claim 17, wherein the at least one physiological characteristic comprises a degree of brown adipose tissue thermogenesis occurrence.

21. The apparatus of claim 17, wherein the at least one physiological characteristic comprises a core temperature of the at least one experimental animal.

* * * * *